(12) United States Patent
Takatsuka et al.

(10) Patent No.: US 7,300,645 B2
(45) Date of Patent: Nov. 27, 2007

(54) ORAL COMPOSITION COMPRISING ISOMALT AND REMINERALIZING ENHANCING AGENT

(75) Inventors: Tsutomu Takatsuka, Osaka (JP); Akira Nakao, Osaka (JP)

(73) Assignee: Sunstar Kabushiki Kaisha, Osaka (JP)

( * ) Notice: Subject to any disclaimer, the term of this patent is extended or adjusted under 35 U.S.C. 154(b) by 0 days.

(21) Appl. No.: 10/279,117

(22) Filed: Oct. 24, 2002

(65) Prior Publication Data

US 2003/0170185 A1 Sep. 11, 2003

Related U.S. Application Data

(62) Division of application No. 09/673,618, filed as application No. PCT/JP99/02060 on Apr. 19, 1999, now Pat. No. 6,471,946.

(30) Foreign Application Priority Data

| Apr. 24, 1998 | (JP) | 1998/131413 |
| Dec. 28, 1998 | (JP) | 1998/373873 |
| Apr. 15, 1999 | (JP) | 1999/107809 |

(51) Int. Cl.
 A61K 8/21 (2006.01)
 A61K 8/30 (2006.01)
 A61Q 11/00 (2006.01)
(52) U.S. Cl. .................. 424/52; 424/49; 514/835; 514/901
(58) Field of Classification Search ............ 424/49–58, 424/641, 642, 643; 426/658, 660; 514/53, 514/54, 835
See application file for complete search history.

(56) References Cited

U.S. PATENT DOCUMENTS

| 4,022,880 A | * | 5/1977 | Vinson et al. ................ 424/49 |
| 4,100,269 A | * | 7/1978 | Pader .......................... 424/49 |
| 4,289,755 A | | 9/1981 | Dhabhar |
| 4,356,168 A | * | 10/1982 | Harvey et al. ................ 424/52 |
| 4,396,599 A | | 8/1983 | Sipos |
| 4,425,324 A | * | 1/1984 | Harvey et al. ................ 424/52 |
| 4,522,806 A | | 6/1985 | Muhlemann et al. |
| 4,562,066 A | * | 12/1985 | Hayes et al. ................. 424/52 |
| 4,587,119 A | * | 5/1986 | Bucke et al. |
| 5,089,255 A | * | 2/1992 | Gaffar et al. ................. 424/52 |
| 5,370,881 A | * | 12/1994 | Fuisz ........................... 426/5 |
| 5,372,802 A | * | 12/1994 | Barrows et al. .............. 424/52 |
| 5,455,024 A | * | 10/1995 | Winston et al. .............. 424/52 |
| 5,629,040 A | | 5/1997 | Takemori et al. ............ 426/548 |
| 5,645,853 A | * | 7/1997 | Winston et al. ............. 424/440 |
| 5,698,181 A | * | 12/1997 | Luo |
| 5,731,936 A | | 3/1998 | Lee et al. |
| 5,768,067 A | | 6/1998 | Saito et al. |
| 5,773,604 A | * | 6/1998 | Lefevre et al. .............. 536/104 |
| 5,784,225 A | | 7/1998 | Saito et al. |
| 5,785,957 A | * | 7/1998 | Losee et al. |
| 5,833,957 A | * | 11/1998 | Winston et al. .............. 424/49 |
| 5,861,169 A | * | 1/1999 | Kaufmann |
| 6,046,892 A | | 4/2000 | Aoshima et al. |
| 6,080,481 A | * | 6/2000 | Ochs et al. .................. 132/321 |
| 6,120,754 A | * | 9/2000 | Lee et al. ..................... 424/49 |
| 6,177,064 B1 | * | 1/2001 | de Troostembergh et al. ............................ 424/49 |
| 6,197,288 B1 | * | 3/2001 | Mankoo ....................... 424/49 |
| 6,224,904 B1 | | 5/2001 | Rapp et al. |

FOREIGN PATENT DOCUMENTS

| EP | 0 074 082 | | 3/1983 |
| EP | 0 251 146 A2 | | 1/1988 |
| EP | 800823 A | * | 10/1997 |
| EP | 0 809 939 | | 12/1997 |
| EP | 0 809 939 A1 | | 12/1997 |
| JP | 52-61236 | | 10/1976 |
| JP | 57-32219 | | 2/1982 |
| JP | 57-108007 | | 7/1982 |
| JP | 58-46012 | | 3/1983 |
| JP | 58-62109 | | 4/1983 |
| JP | 60-204710 | | 10/1985 |
| JP | 60204710 | * | 10/1985 |
| JP | 63-008324 | | 1/1988 |
| JP | 63-045215 | | 2/1988 |
| JP | 03-048613 | | 3/1991 |
| JP | 05-097668 | | 4/1993 |
| JP | 6-070704 | | 3/1994 |
| JP | 7-132047 | | 5/1995 |
| JP | 8-88118 | | 7/1996 |
| JP | 8-214774 | | 8/1996 |
| JP | 9-000199 | | 1/1997 |
| JP | 9-69211 | | 3/1997 |
| JP | 9-107900 | | 4/1997 |
| JP | 9-238642 | | 9/1997 |
| JP | 10-155410 | | 6/1998 |
| JP | 11-191647 | | 7/1999 |

(Continued)

OTHER PUBLICATIONS

Grenby et al Oral Diseases 2(1):32-40 Sweets reformulated to improve dental properties Imfeld Schw. Monat. Zahn Med 104 (8)-941-945 Clinical Caries Studies With Poly Alcohols, Mar. 1996-1994.*

(Continued)

Primary Examiner—Frederick Krass
(74) Attorney, Agent, or Firm—Foley and Lardner LLP

(57) ABSTRACT

Disclosed is an oral composition comprising palatinit. More particularly, disclosed is an oral composition comprising palatinit which exerts a synergistic effect when combined with a fluorine or zinc compound.

13 Claims, 2 Drawing Sheets

FOREIGN PATENT DOCUMENTS

| | | | |
|---|---|---|---|
| WO | 9202149 | * | 2/1992 |
| WO | WO93/08699 A1 | | 5/1993 |
| WO | WO98/12936 A1 | | 4/1998 |

OTHER PUBLICATIONS

Imfeld Caries Research 27 Suppl 1 50-5 Efficacy of Sweeteners and Sugar Substitutes in Caries Prevention Makinen et al Progress in Food & Nutrition Sci. 12(1): 73-109, 1993-1998.*

Birkhed et al Int. Dental Journal 35(1): 9-17 Microbiological Aspects of Some Caloric Sugar Substitutes, Mar. 1985.*

Edgar et al Int. Dental Journal 35(1): 18-22 The Effect of Sweeteners on Acid Prevention in Plaque, Mar. 1985.*

Arends et al., "Combined Effect of Xylitol and Fluoride on Enamel Demineralization in Vitro," Caries Res. vol. 24, S. Karger AG, 1990, pp. 256-257.

Arends, "Influence of Xylitol-and/or Fluoride-Containing Toothpastes on the Remineralization of Surface Softened Enamel Defects in Vivo," Caries Res., vol. 19, S. Karger AG, 1985, pp. 528-535.

Partial English Translation of Journal of Dental Health, vol. 46, 1996, pp. 442-443.

* cited by examiner

ORAL COMPOSITION COMPRISING ISOMALT AND REMINERALIZING ENHANCING AGENT

CROSS-REFERENCE TO RELATED APPLICATIONS

This application is a divisional of application Ser. No. 09/673,618, filed Oct. 19, 2000, now U.S. Pat. No. 6,471,946 which is a national phase application from PCT/JP99/02060, filed Apr. 19, 1999 and claims the benefit of priority under 35 U.S.C. § 119(e) of the above applications and Japanese patent application nos. JP 131413, filed Apr. 24, 1009, JP 373873, filed Dec. 28, 1998, and JP 107809, filed Apr. 15, 1999, the disclosures of which are incorporated herein in their entirety.

FIELD OF THE INVENTION

The present invention relates to an oral composition comprising palatinit, and more particularly, it relates to an oral composition comprising palatinit which exhibits the synergistic effect when combined with a fluorine or zinc compound.

BACKGROUND OF THE INVENTION

Dental caries is a state of a dental carious cavity caused by the dissolution of calcium from teeth and which can not naturally return to a healthy state. But, there is a state referred to as a sub-surface lesion which can return to the healthy state, in the course of the development of the dental carious cavity ("Zusetsu Ushoku-gaku" edited by Shoichi, Suga, 1990, 139). Therefore, in order to decrease dental caries, it is desirable to enhance the remineralization so that the teeth can return to the healthy state within a term during which the teeth return to the original state.

As a method for enhancing the remineralization, the use of fluorine compounds has been known for a long time. However, because the ingestion of a large amount of fluorine exhibits the toxicity, it is desired that fluorine be effectively utilized in an as smaller as possible amount. To accomplish this, the use of a substance that enhances the remineralization effect of fluorine is exemplified. For example, there is proposed a combination of fluorine and hydroxy-apatite in JP-A-1-110608. However, its effect is insufficient and is not satisfactory.

On the other hand, a zinc compound that has been utilized in the oral composition generally has an astringent or salty taste and, therefore, there is a problem that it has the very bad feeling for use upon its use.

One object of the present invention is to provide an oral composition which has the high safety and can enhance the remineralization. Another object of the present invention is to provide an oral composition which exhibits the sufficient remineralization effect and has the better feeling for use.

SUMMARY OF THE INVENTION

In view of the above circumstances, the present inventors studied intensively the substances that can enhance the remineralization and, as a result, found that palatinit exhibits the excellent properties, that an oral composition comprising palatinit can enhance the remineralization, and, further, that the inclusion of palatinit in a combination with a fluorine or zinc compound can enhance the remineralization due to the synergistic effect of both ingredients, which resulted in the completion of the present invention.

Palatinit has hitherto been utilized in foods and the like as a low cariogenic sweetener. However, palatinit has never been utilized for an oral-use, and its remineralization effect is not known.

That is, the present invention has completed based on such novel findings, and, in the first aspect, provides an oral composition comprising palatinit which has the high safety and can enhance the remineralization.

Moreover, in the second aspect, the present invention provides an oral composition comprising palatinit and a remineralization enhancing ingredient, which exhibits the sufficient remineralization effect and has the better feeling for use.

The present invention is described below in detail according to the first and second aspects thereof in sequence.

[First Aspect]

Palatinit to be used in the first and second aspects of the present invention is a sugar alcohol of a disaccharide, and may be α-D-glucopyranosyl-1,6-mannitol, its isomer, α-D-glucopyranosyl-1,6-sorbitol or a mixture thereof. Palatinit can be obtained by hydrogenation of palatinose which is converted from sucrose as a raw material with glycosyl-transferase. And, palatinit is also a trade name of the product of Mitsui Sugar Co. Ltd. or Sudzucker A. G., and is also referred to as reduced-palatinose or isomalt. Palatinit is widely known as a non-cariogenic sugar which scarcely develops dental caries, based on the fact that the cariogenic microorganisms do not produce acids from palatinit in an oral cavity. Palatinit has been blended in non-sugar foods or a specified health food such as so-called "dental caries-resistant candy".

The amount of palatinit to be blended in the present oral composition is in the range of 0.1% to 60% by weight, preferably 1% to 40% by weight, based on the total weight of the oral composition. When the amount is less than 0.1% by weight, the desired effect can not be obtained. On the other hand, when the amount is more than 60% by weight, the stability of the formulation is deteriorated.

[Second Aspect]

The remineralization enhancing ingredient to be used in the second aspect of the present invention is an ingredient which can remineralize the teeth from its sub-surface lesion state. Examples of the remineralization enhancing ingredient are fluorine compounds, zinc compounds, phosphorus compounds, calcium compounds and the like, but not limited thereto.

Examples of the fluorine compound to be used in the second aspect of the present invention as the remineralization enhancing ingredient are sodium fluoride, potassium fluoride, ammonium fluoride, stannous fluoride, sodium or potassium monofluorophosphate and the like. Particularly preferred are sodium fluoride and sodium monofluorophosphate.

These fluorine compounds, alone or in a combination thereof, may be blended in the present oral composition in the range of 0.1-5,000 ppm, preferably 100-1,100 ppm in terms of fluoride ion, based on the total weight of the present oral composition.

Further, the zinc compound to be used in the second aspect of the present invention as the remineralization enhancing ingredient is preferably a water-slightly soluble zinc compound, wherein the water-slightly soluble zinc compound is defined as having the solubility of less than 0.5 g per 100 g of water at 25, and water-insoluble zinc compound is included therein. Among them, particularly preferred are zinc oxide, zinc citrate and zinc stearate. From a viewpoint of a taste, the water-slightly soluble zinc compound having a smaller particle diameter and a greater specific surface area is preferred. More particularly, preferred are those having the particle diameter of not greater than 0.3 µm and the specific surface area of greater than 10 $m^2/g$. When the particle diameter exceeds 0.3 µm, the astringency becomes strong. Examples of the commercial products of the zinc compound are fine particle zinc white and hyperfine particle zinc oxide, "FINEX series" manufactured by Sakai Chemical Industry Co., Ltd. These water-slightly soluble zinc compounds, alone or in a combination thereof, may be blended in the oral composition in the amount of 0.1% to 5% by weight, based on the total weight of the present oral composition.

Further, when the oral composition of the second aspect of the present invention contains a zinc compound, preferred pH thereof is within the range of 6.0 to 8.5. When pH is lower than 6.0, then the astringency is strong, and when pH is higher than 8.5, then oral mucosa may be irritated, therefore, the composition out of the above pH range is not preferable.

Further, examples of the phosphorus compound to be used in the second aspect of the present invention as the remineralization enhancing ingredient are disodium hydrogenphosphate, sodium dihydrogenphosphate, dipotassium hydrogenphosphate, potassium dihydrogenphosphate, trisodium phosphate, tripotassium phosphate and the like, but not limited thereto.

Moreover, examples of the calcium compound to be used in the second aspect of the present invention as the remineralization enhancing ingredient are, for example, calcium chloride, calcium nitrate, calcium sulfate, calcium carbonate, calcium citrate, calcium hydrogenpyrophosphate, calcium gluconate, calcium glycerophosphate, calcium hydroxide, calcium oxide, calcium silicate and the like, but not limited thereto.

That is, the present invention provides an oral composition comprising palatinit alone or in a combination with any remineralization enhancing ingredients, which can enhance the remineralization due to the synergistic effect of both ingredients.

The oral composition of the present invention may be properly formulated, depending upon its use, into a form such as a toothpaste, powder or liquid dentifrice, wetting dentifrice, gel, cream, pasta, mouthwash, spray, foam, coating agent and the like, according to the conventional procedure. Other ingredients to be blended therein are not particularly limited, and the known active ingredients, polishing agents, humectants, thickening agents, foaming agents, preservatives, flavoring agents, sweeteners, pH adjusting agents, organic acids, sugar alcohol, anti-oxidizing agents and others known as the ingredient for the oral composition may be blended in the oral composition, so long as they do not deteriorate the effects of the present invention.

Examples of the active ingredient are enzymes such as amylase, protease, lysozyme and dextranase, the antimicrobial agents such as sanguinarine, allantoin, aminobenzoate derivatives, hexetidine, chlorhexidine, triclosan and cetylpyridinium chloride, vitamins such as vitamin B, C and E, and the astringents such as potassium nitrate, lithium nitrate and sodium nitrate.

Examples of the polishing agent are silica, alumina, aluminosilicate, aluminium hydroxide and the like.

Examples of the humectant are glycerol, propylene glycol, sorbitol, polyethylene glycol, polypropylene glycol and the like.

Examples of the thickening agent are sodium carboxymethyl cellulose, methyl cellulose, hydroxyethyl cellulose, alginates, xanthan gum, carrageenan, gum arabic, polyvinyl alcohol and the like.

Examples of the forming agent are anionic-, nonionic-, cationic- and amphoteric-surfactants. Examples of the anionic-surfactant are alkyl sulfates, sodium dodecylbenzene sulfonate, amino acids, sulfosuccinates, sucrose fatty acid esters and the like. Examples of the nonionic-surfactant are Pluronic series that are polyoxyethylene-polyoxypropylene copolymer, fatty acid dialkanolamides and the like.

Examples of the preservative are methylparaben, propylparaben, benzoates, sodium benzoate, paraoxybenzoic acid esters, titanium dioxide and the like.

Examples of the flavoring agent are peppermint oil, spearmint oil, Japanese peppermint oil, orange oil, menthol, cloves oil, anise oil, wintergreen oil, eucalyptus oil and the like.

Examples of the sweetening agent or sweetener are saccharin salts, dextrose, Aspartame, xylitol, stevia extract, Acesulfame, granulated sugar, powdered sugar, starch syrup and the like. Although palatinit exhibits sweetness, the above sweetening agents or sweeteners may be added depending upon the feeling for use of the formulation.

Examples of the pH adjusting agent are citric acid and salts thereof, phosphoric acid and salts thereof, malic acid and salts thereof, gluconic acid and salts thereof, maleic acid and salts thereof, aspartic acid and salts thereof, gluconic acid and salts thereof, succinic acid and salts thereof, glucuronic acid and salts thereof, fumaric acid and salts thereof, glutamic acid and salts thereof, adipic acid and salts thereof, lactic acid and salts thereof, pantothenic acid and salts thereof, hydrochloric acid, alkali metal hydroxides and the like.

DETAILED DESCRIPTION OF THE INVENTION

The present invention will be further illustrated by way of the following Examples, which are not to be construed to limit the scope of the present invention. The amounts indicated in the Examples are all percents (%) by weight.

EXPERIMENTAL EXAMPLE 1

Evaluation of the Remineralizing Ability 1

The remineralization effect of the sugars was evaluated in an in vitro test using a bovine tooth according to the procedures described in D. J. White et al., *Caries Res.*, 21, 228 (1987).

1. An enamel section having 4 mm length×3 mm width was obtained from the bovine tooth. The section was embedded in a dental resin to obtain an enamel block.

2. An enamel varnish was applied to a portion of approximately ⅓ of the surface of the enamel block in order not to cause the demineralization of that portion. Then, the enamel block was demineralized with a demineralizing solution containing 50% of saturated hydroxyapatite/0.1M lactic acid/pH 5.0 to prepare an artificial caries.

3. An enamel varnish was applied to a portion of approximately ⅔ of the surface of the treated enamel block in order not to cause the remineralization of that portion. The enamel block was immersed for ten days in a test solution prepared by adding the test sugar into an aqueous solution containing 3.0 mM calcium ion and 1.8 mM phosphate ion so that the concentration of the sugar became 20%, to perform the remineralization treatment.

4. Three thin sections having approximately 500 μm in thickness were prepared from the enamel block. The central portion of the thin sections was ground so that the thickness became approximately 100 μm using a double-side polishing machine.

Figure 1:
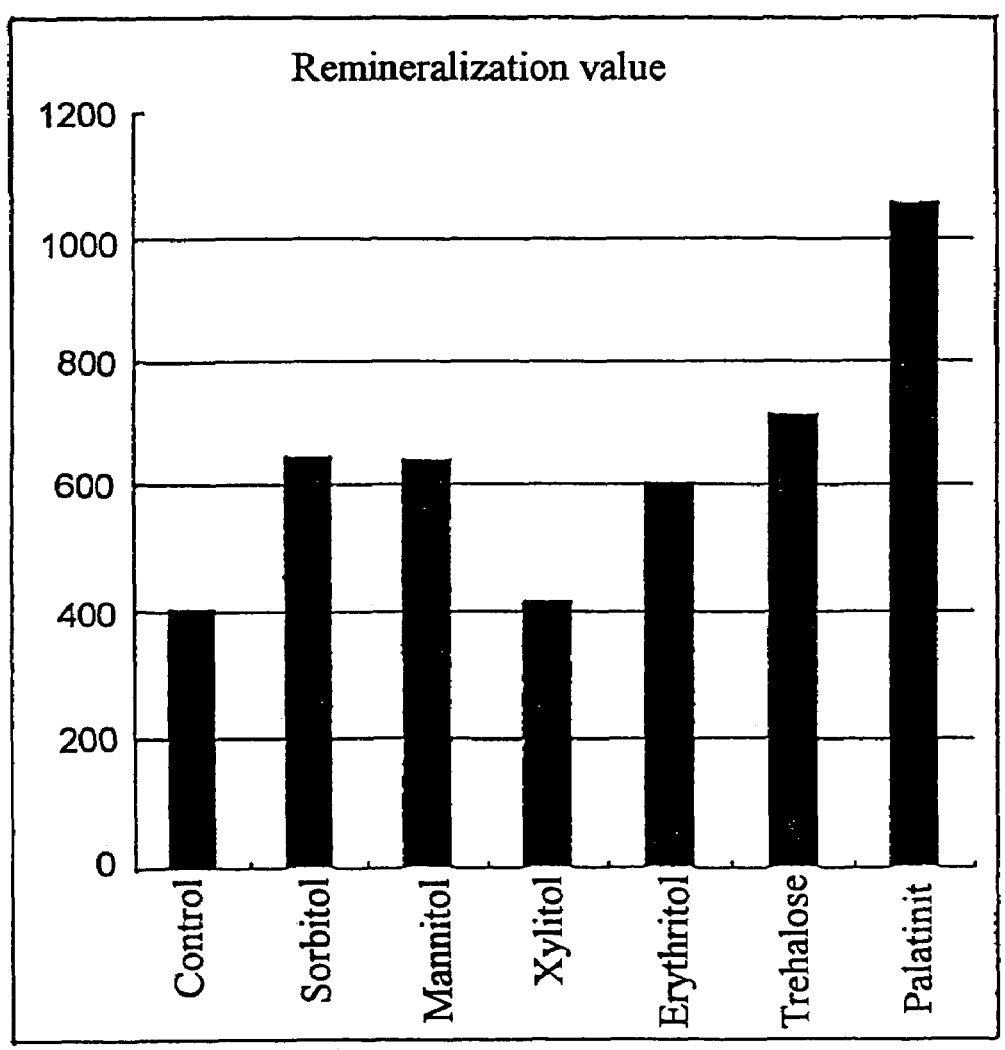
FIG. 1 is a graph which compares the remineralization effects of the various sugars in the system not containing fluoride.

5. The X-ray photograph was taken of the thin section prepared in the fourth step. The mineral amounts of the demineralized portion and the remineralized portion were calculated based on the brightness of the each portion and a distance from the surface using an image processor. The mineral amount difference between the demineralized and remineralized portions was expressed as a remineralization value. A greater value thereof shows the greater remineralization. A control test was performed in a similar manner to that described above, except that the test solution containing only 3.0 mM calcium ion and 1.8 mM phosphate ion but not containing the sugar was used. The results are shown in Table 1 and FIG. 1.

TABLE 1

| Systems not containing fluoride | |
|---|---|
| Sugar (20%) | Remineralization value |
| Control | 405 |
| Sorbitol | 645 |
| Mannitol | 640 |
| Xylitol | 416 |
| Erythritol | 602 |

TABLE 1-continued

| Systems not containing fluoride | |
|---|---|
| Sugar (20%) | Remineralization value |
| Trehalose | 715 |
| Palatinit | 1057 |

Unit: Vol. % μm

Figure 2:
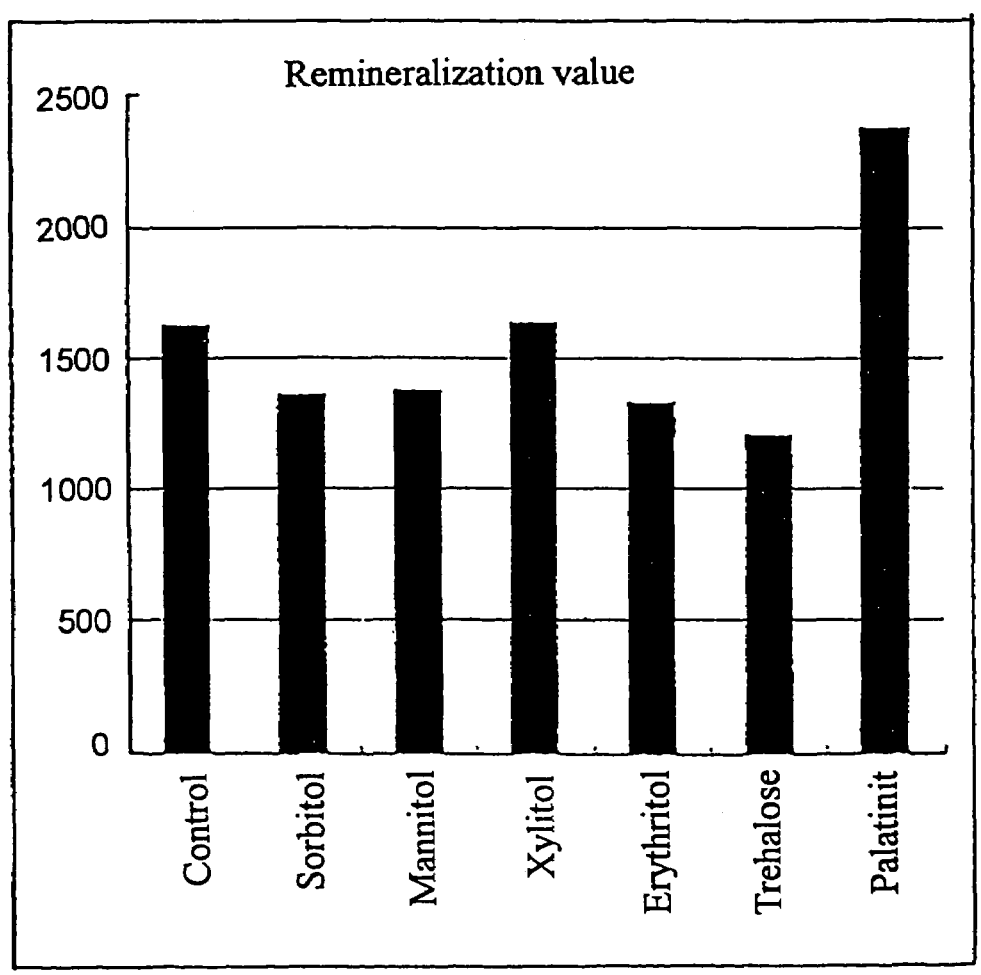
FIG. 2 is a graph which compares the remineralization effects of the various sugars in the system containing fluoride.

Further, a similar test was performed in which sodium fluoride was added to the test solution to 2 ppm in terms of fluoride ion. The results are shown in Table 2 and FIG. 2.

TABLE 2

| Systems containing fluoride (2 ppm) | |
|---|---|
| Sugar (20%) | Remineralization value |
| Control | 1626 |
| Sorbitol | 1358 |
| Mannitol | 1377 |
| Xylitol | 1636 |
| Erythritol | 1330 |
| Trehalose | 1205 |
| Palatinit | 2374 |

Unit: Vol. % μm

From Tables 1 and 2, it was found that, among the sugars tested, palatinit has the particularly excellent remineralizing ability and that the remineralizing ability is enhanced by combining palatinit with sodium fluoride.

EXPERIMENTAL EXAMPLE 2

Evaluation of the Remineralizing Ability 2

The remineralization enhancing effects of the oral compositions to which the various sugars had been added were tested in vitro according to the similar manner to that described in Experimental Example 1.

Provided that, in the remineralization treatment, a solution containing 3.0 mM calcium ion and 1.8 mM phosphate ion to which a test dentifrice (see Table 3) had been added as to form a 4-fold slurry was used, and the immersion period was set to be fourteen days. The results of the X-ray photograph were evaluated using the image processor according to a similar manner to that described in Experimental Example 1. The results are shown in Table 3.

TABLE 3

| Ingredients | Example 1 | Example 2 | Example 3 | Example 4 | Example 5 | Example 6 | Comparative Example 1 | Comparative Example 2 | Comparative Example 3 | Comparative Example 4 | Comparative Example 5 |
|---|---|---|---|---|---|---|---|---|---|---|---|
| Silicic acid anhydride | 20 | 20 | 20 | 20 | 20 | 20 | 20 | 20 | 20 | 20 | 20 |
| Sodium carboxymethyl cellulose | 1.5 | 1.5 | 1.5 | 1.5 | 1.5 | 1.5 | 1.5 | 1.5 | 1.5 | 1.5 | 1.5 |
| Sorbitol | 40 | 40 | 35 | 25 | 15 | 15 | 45 | 45 | 35 | 35 | 35 |
| Sodium lauryl sulfate | 1.5 | 1.5 | 1.5 | 1.5 | 1.5 | 1.5 | 1.5 | 1.5 | 1.5 | 1.5 | 1.5 |
| Saccharin sodium | 0.1 | 0.1 | 0.1 | 0.1 | 0.1 | 0.1 | 0.1 | 0.1 | 0.1 | 0.1 | 0.1 |
| Sodium fluoride | — | 0.2 | 0.2 | 0.2 | 0.2 | 0.2 | — | 0.2 | 0.2 | 0.2 | 0.2 |
| Flavor | 1 | 1 | 1 | 1 | 1 | 1 | 1 | 1 | 1 | 1 | 1 |

TABLE 3-continued

| Ingredients | Example 1 | Example 2 | Example 3 | Example 4 | Example 5 | Example 6 | Comparative Example 1 | Comparative Example 2 | Comparative Example 3 | Comparative Example 4 | Comparative Example 5 |
|---|---|---|---|---|---|---|---|---|---|---|---|
| Xylitol | — | — | — | — | — | — | — | — | 10 | — | — |
| Erythritol | — | — | — | — | — | — | — | — | — | 10 | — |
| Trehalose | — | — | — | — | — | — | — | — | — | — | 10 |
| Palatinit | 10 | 5 | 10 | 20 | 30 | 60 | — | — | — | — | — |
| Remineralization value | 852 | 1328 | 1468 | 1496 | 1548 | 1580 | 320 | 1024 | 958 | 842 | 862 |

From the above Table 3, it was found that palatinit has particularly excellent remineralizing ability, also in the evaluation of Examples 1-6 and Comparative Examples 1-5.

EXPERIMENTAL EXAMPLE 3

Evaluation of the Remineralizing Ability 3

The remineralization enhancing effect of the oral composition to which the zinc compound had been added was tested in vitro according to almost the same manner as that described in Experimental Example 1.

Provided that, in the remineralization treatment, a solution containing 3.0 mM calcium ion and 1.8 mM phosphate ion to which the test dentifrice (see Table 4) had been added so as to form a 4-fold slurry was used, and the pH cycling procedure was taken in which the enamel block was additionally immersed in the demineralization solution for three hours per day. An evaluation period was set to be fourteen days. The results of the X-ray photograph were evaluated using the image processor according to a similar manner to that described in Experimental Example 1. The results are shown in Table 4.

From the above Table 4, in the evaluation of Examples 7-13 and Comparative Examples 6-7, it was shown that the remineralization is enhanced by blending palatinit and a zinc compound.

EXPERIMENTAL EXAMPLE 4

Organoleptic Evaluation of the Astringency 1

The oral compositions of Examples 14-16 and Comparative Examples 8-9 in Table 5 were prepared. Ten healthy persons used these oral compositions according to the conventional manner, and the astringency after spout was organoleptically evaluated. The total points of ten healthy persons are shown according to the following 3 grades—criteria: 2: excellent; 1: good; 0: astringent. The results are shown in Table 5.

TABLE 4

| Ingredients | Example 7 | Example 8 | Example 9 | Example 10 | Example 11 | Example 12 | Example 13 | Comparative Example 6 | Comparative Example 7 |
|---|---|---|---|---|---|---|---|---|---|
| Silicic acid anhydride | 20 | 20 | 20 | 20 | 20 | 20 | 20 | 20 | 20 |
| Sodium carboxymethyl cellulose | 1.5 | 1.5 | 1.5 | 1.5 | 1.5 | 1.5 | 1.5 | 1.5 | 1.5 |
| Sorbitol | 40 | 40 | 35 | 25 | 35 | 35 | 35 | 50 | 35 |
| Sodium lauryl sulfate | 1.5 | 1.5 | 1.5 | 1.5 | 1.5 | 1.5 | 1.5 | 1.5 | 1.5 |
| Saccharin sodium | 0.1 | 0.1 | 0.1 | 0.1 | 0.1 | 0.1 | 0.1 | 0.1 | 0.1 |
| Sodium fluoride | — | 0.2 | 0.2 | 0.2 | 0.2 | 0.2 | 0.2 | — | 0.2 |
| Flavor | 1 | 1 | 1 | 1 | 1 | 1 | 1 | 1 | 1 |
| Xylitol | — | — | — | — | — | — | — | — | 10 |
| Palatinit | 10 | 10 | 10 | 20 | 10 | 10 | 10 | — | — |
| Zinc oxide | 1 | — | 1 | — | — | 0.1 | 5 | 1 | — |
| Zinc stearate | — | — | — | 1 | — | — | — | — | — |
| Zinc citrate | — | — | — | — | 1 | — | — | — | — |
| Remineralization value | 102 | 513 | 542 | 516 | 630 | 530 | 721 | 10 | 354 |

TABLE 5

| Ingredients | Example 14 | Example 15 | Example 16 | Comparative Example 8 | Comparative Example 9 |
|---|---|---|---|---|---|
| Silicic acid anhydride | 20 | 20 | 20 | 20 | 20 |
| Sodium carboxymethyl cellulose | 1.5 | 1.5 | 1.5 | 1.5 | 1.5 |
| Sorbitol | 35 | 35 | 35 | 35 | 35 |
| Sodium lauryl sulfate | 1.5 | 1.5 | 1.5 | 1.5 | 1.5 |
| Saccharin sodium | 0.1 | 0.1 | 0.1 | 0.1 | 0.1 |
| Sodium fluoride | 0.2* | 0.2 | 0.2 | 0.2 | 0.2 |
| Flavor | 1 | 1 | 1 | 1 | 1 |
| Zinc oxide 1 | 1 | — | — | 1 | — |
| Zinc oxide 2 | — | 1 | — | — | — |
| Zinc oxide 3 | — | — | 1 | — | 1 |
| Palatinit | 10 | 10 | 10 | — | — |
| Total point | 15 | 17 | 17 | 0 | 2 |

*The concentration in terms of fluoride ion is 905 ppm.
Zinc oxide 1: The average particle diameter is 0.5 μm and the specific surface area is 8 $m^2/g$.
Zinc oxide 2: The average particle diameter is 0.28 μm and the specific surface area is 10 $m^2/g$.
Zinc oxide 3: The average particle diameter is 0.04 μm and the specific surface area is 25 $m^2/g$.

From the above Table 5, it was found that the astringency can be improved by decreasing the average particle diameter of zinc oxide or increasing the specific surface area thereof, and can be further improved by combining with palatinit.

EXPERIMENTAL EXAMPLE 5

Organoleptic Evaluation of the Astringency 2

The oral compositions of Examples 17-18 and Comparative Example 10 having the varied pH values were prepared, and evaluated according to a similar manner to that described above. The results are shown in Table 6.

TABLE 6

| Ingredients | Example 17 | Example 18 | Comparative Example 10 |
|---|---|---|---|
| Silicic acid anhydride | 20 | 20 | 20 |
| Sodium carboxymethyl cellulose | 1.5 | 1.5 | 1.5 |
| Sorbitol | 35 | 35 | 35 |
| Sodium lauryl sulfate | 1.5 | 1.5 | 1.5 |
| Saccharin sodium | 0.1 | 0.1 | 0.1 |
| Sodium fluoride | 0.2 | 0.2 | 0.2 |
| Flavor | 1 | 1 | 1 |
| Zinc oxide 2* | 1 | 1 | 1 |
| Palatinit | 10 | 10 | 10 |
| Disodium hydrogenphosphate | 0.1 | 0.1 | 0.1 |
| Sodium dihydrogenphosphate | 0.25 | 0.2 | 0.3 |
| pH | 6.0 | 7.0 | 5.0 |
| Total point | 16 | 17 | 10 |

*The average particle diameter is 0.28 μm and the specific surface area is 10 $m^2/g$.

From the above Table 6, it was shown that the astringency can be improved by adjusting pH of the oral composition to 6.0 or higher.

EXAMPLE 19 TOOTHPASTE

A toothpaste was prepared by the following formulation according to the conventional procedures.

| Ingredients | Amounts % |
|---|---|
| Palatinit | 10.0 |
| Sodium fluoride | 0.2 |
| (The concentration in terms of fluoride ion is 905 ppm) | |
| Silicic acid anhydride | 16.0 |
| Sodium carboxymethyl cellulose | 1.3 |
| Sodium lauryl sulfate | 1.0 |
| Titanium dioxide | 0.4 |
| Paraoxybenzoic acid ester | 0.1 |
| Citric acid | 0.1 |
| Trisodium citrate | 0.3 |
| Saccharin sodium | 0.1 |
| Flavor | 0.6 |
| Sorbitol | 50.0 |
| Purified water | balance |
| Total | 100.0 |

EXAMPLE 20 TOOTHPASTE

A toothpaste was prepared by the following formulation according to the conventional procedures.

| Ingredients | Amounts % |
|---|---|
| Palatinit | 30.0 |
| Silicic acid anhydride | 20.0 |
| Sodium carboxymethyl cellulose | 1.2 |
| Sodium lauryl sulfate | 1.2 |
| Titanium dioxide | 0.3 |
| Hydrochloric acid | 0.5 |
| Saccharin sodium | 0.13 |
| Sorbitol | 10.0 |
| Flavor | 1.0 |
| Purified water | balance |
| Total | 100.0 |

EXAMPLE 21 TOOTHPASTE

A toothpaste was prepared by the following formulation according to the conventional procedures.

| Ingredients | Amounts % |
| --- | --- |
| Palatinit | 50.0 |
| Sodium fluoride | 0.2 |
| (The concentration in terms of fluoride ion is 905 ppm) | |
| Silicic acid anhydride | 16.0 |
| Carrageenan | 1.3 |
| Sodium lauryl sulfate | 3.5 |
| Titanium dioxide | 0.4 |
| Paraben | 0.1 |
| Xylitol | 10.0 |
| Flavor | 0.7 |
| Glycerol | 5.0 |
| Purified water | balance |
| Total | 100.0 |

EXAMPLE 22 TOOTHPASTE

A toothpaste was prepared by the following formulation according to the conventional procedures.

| Ingredients | Amounts % |
| --- | --- |
| Palatinit | 15.0 |
| Sodium monofluorophosphate | 0.76 |
| (The concentration in terms of fluoride ion is 950 ppm) | |
| Calcium carbonate | 16.0 |
| Sodium carboxymethyl cellulose | 1.3 |
| Sodium lauroylsarcosinate | 2.0 |
| Polyoxyethylene hydrogenated castor oil | 1.0 |
| Titanium dioxide | 0.4 |
| Paraoxybenzoic acid ester | 0.1 |
| Malic acid | 0.2 |
| Stevia extract | 0.1 |
| Flavor | 0.7 |
| Sorbitol | 40.0 |
| Polyethylene glycol | 5.0 |
| Purified water | balance |
| Total | 100.0 |

EXAMPLE 23 TOOTHPASTE

A toothpaste was prepared by the following formulation according to the conventional procedures.

| Ingredients | Amounts % |
| --- | --- |
| Palatinit | 5.0 |
| Sodium fluoride | 0.21 |
| (The concentration in terms of fluoride ion is 950 ppm) | |
| Triclosan | 0.5 |
| Silicic acid anhydride | 16.0 |
| Sodium polyacrylate | 2.0 |
| Sodium lauryl sulfate | 1.0 |
| Pluronic | 1.0 |
| Titanium dioxide | 0.4 |
| Paraoxybenzoic acid ester | 0.1 |
| Xylitol | 10.0 |
| Flavor | 0.7 |
| Sorbitol | 50.0 |
| Purified water | balance |
| Total | 100.0 |

EXAMPLE 24 MOUTHWASH

A mouthwash was prepared by the following formulation according to the conventional procedures.

| Ingredients | Amounts % |
| --- | --- |
| Palatinit | 10.0 |
| Sodium fluoride | 0.05 |
| (The concentration in terms of fluoride ion is 225 ppm) | |
| Sodium lauryl sulfate | 0.5 |
| Polyoxyethylene hydrogenated castor oil | 1.0 |
| Sodium dihydrogenphosphate | 0.1 |
| Disodium hydrogenphophate | 0.1 |
| Saccharin sodium | 0.1 |
| Flavor | 0.7 |
| Ethanol | 10.0 |
| Glycerol | 10.0 |
| Purified water | balance |
| Total | 100.0 |

EXAMPLE 25 MOUTHWASH

A mouthwash was prepared by the following formulation according to the conventional procedures.

| Ingredients | Amounts % |
| --- | --- |
| Palatinit | 30.0 |
| Polyoxyethylene hydrogenated castor oil | 1.0 |
| Sodium citrate | 0.2 |
| Citric acid anhydride | 0.2 |
| Flavor | 0.8 |
| Glycerol | 10.0 |
| Purified water | balance |
| Total | 100.0 |

EXAMPLE 26 MOUTHWASH

A mouthwash was prepared by the following formulation according to the conventional procedures.

| Ingredients | Amounts % |
| --- | --- |
| Palatinit | 10.0 |
| Sodium fluoride | 0.05 |
| (The concentration in terms of fluoride ion is 225 ppm) | |
| Sodium lauryl sulfate | 0.2 |
| Polyoxyethylene (2)-synthetic $C_{12}$, $C_{14}$ alkyl-sodium sulfosuccinate | 0.2 |
| Malic acid | 0.3 |
| Flavor | 0.7 |
| Glycerol | 10.0 |
| Xylitol | 5.0 |
| Purified water | balance |
| Total | 100.0 |

EXAMPLE 27 GEL DENTIFRICE

A gel dentifrice was prepared by the following formulation according to the conventional procedures.

| Ingredients | Amounts % |
| --- | --- |
| Palatinit | 10.0 |
| Hydroxyethyl cellulose | 3.0 |
| Sodium fluoride | 1.0 |
| (The concentration in terms of fluoride ion is 4,500 ppm) | |
| Phosphoric acid | 3.0 |
| Saccharin sodium | 0.5 |
| Flavor | 0.8 |
| Glycerol | 20.0 |
| Purified water | balance |
| Total | 100.0 |

EXAMPLE 28 NON AEROSOL-TYPE FOAM DENTIFRICE

A non aerosol-type foam dentifrice was prepared by the following formulation according to the conventional procedures.

| Ingredients | Amounts % |
| --- | --- |
| Palatinit | 5.0 |
| Sodium fluoride | 1.0 |
| (The concentration in terms of fluoride ion is 4,500 ppm) | |
| Phosphoric acid | 3.0 |
| Tripotassium phosphate trihydrate | 1.5 |
| Sodium lauryl sulfate | 1.0 |
| Pluronic | 7.0 |
| Coconut oil fatty acid diethanolamide | 0.5 |
| Saccharin sodium | 0.8 |
| Flavor | 0.7 |
| Ethanol | 5.0 |
| Purified water | balance |
| Total | 100.0 |

EXAMPLE 29 ORAL GEL

An oral gel was prepared by the following formulation according to the conventional procedures.

| Ingredients | Amounts % |
| --- | --- |
| Palatinit | 20.0 |
| Carboxymethyl cellulose | 0.2 |
| Glycerol | 40.0 |
| Grape seed extract | 1.0 |
| α-tocopherol | 0.05 |
| Purified water | balance |
| Total | 100.0 |

EXAMPLE 30 TOOTHPASTE

A toothpaste was prepared by the following formulation according to the conventional procedures.

| Ingredients | Amounts % |
| --- | --- |
| Palatinit | 10.0 |
| Sodium fluoride | 0.21 |
| (The concentration in terms of fluoride ion is 950 ppm) | |
| Silicic acid anhydride | 21.0 |
| Sodium carboxymethyl cellulose | 1.1 |
| Sodium lauryl sulfate | 0.5 |
| Sodium lauroylsarcosinate | 0.1 |
| Titanium dioxide | 0.3 |
| Fine particle zinc oxide | 1.0 |
| (The average particle diameter is 0.3 μm: the specific surface area is 10 m$^2$/g) | |
| Paraoxybenzoic acid ester | 0.1 |
| Saccharin sodium | 0.1 |
| Flavor | 0.7 |
| Xylitol | 1.0 |
| Sorbitol | 38.0 |
| Hydrochloric acid (2N) | 1.0 |
| Purified water | balance |
| Total | 100.0 |
| pH | 6.5 |

EXAMPLE 31 TOOTHPASTE

A toothpaste was prepared by the following formulation according to the conventional procedures.

| Ingredients | Amounts % |
| --- | --- |
| Palatinit | 50.0 |
| Zinc stearate | 1.0 |
| Sodium fluoride | 0.21 |
| (The concentration in terms of fluoride ion is 950 ppm) | |
| Silicic acid anhydride | 16.0 |
| Carrageenan | 1.3 |
| Sodium lauryl sulfate | 3.5 |
| Titanium dioxide | 0.4 |
| Paraben | 0.1 |
| Xylitol | 10.0 |
| Flavor | 0.7 |
| Glycerol | 5.0 |
| Purified water | balance |
| Total | 100.0 |
| pH | 7.0 |

EXAMPLE 32 TOOTHPASTE

A toothpaste was prepared by the following formulation according to the conventional procedures.

| Ingredients | Amounts % |
| --- | --- |
| Palatinit | 15.0 |
| Zinc citrate | 0.5 |
| Sodium monofluorophosphate | 0.75 |
| (The concentration in terms of fluoride ion is 950 ppm) | |
| Calcium carbonate | 16.0 |
| Sodium carboxymethyl cellulose | 1.3 |
| Sodium lauroylsarcosinate | 2.0 |
| Polyoxyethylene hydrogenated castor oil | 1.0 |

-continued

| Ingredients | Amounts % |
| --- | --- |
| Titanium dioxide | 0.4 |
| Paraoxybenzoic acid ester | 0.1 |
| Malic acid | 0.2 |
| Stevia extract | 0.1 |
| Flavor | 0.7 |
| Sorbitol | 40.0 |
| Polyethylene glycol | 5.0 |
| Purified water | balance |
| Total | 100.0 |
| pH | 7.5 |

EXAMPLE 33 TOOTHPASTE

A toothpaste was prepared by the following formulation according to the conventional procedures.

| Ingredients | Amounts % |
| --- | --- |
| Palatinit | 5.0 |
| Fine particle zinc oxide | 1.5 |
| (The average particle diameter is 0.3 μm: the specific surface area is 10 m$^2$/g.) | |
| Sodium fluoride | 0.21 |
| (The concentration in terms of fluoride ion is 950 ppm) | |
| Triclosan | 0.5 |
| Silicic acid anhydride | 16.0 |
| Sodium polyacrylate | 2.0 |
| Sodium lauryl sulfate | 1.0 |
| Pluronic | 1.0 |
| Titanium dioxide | 0.4 |
| Paraoxybenzoic acid ester | 0.1 |
| Xylitol | 10.0 |
| Flavor | 0.7 |
| Sorbitol | 50.0 |
| Hydrochloric acid (1N) | 1.5 |
| Purified water | balance |
| Total | 100.0 |
| pH | 6.8 |

EXAMPLE 34 MOUTHWASH

A mouthwash was prepared by the following formulation according to the conventional procedures.

| Ingredients | Amounts % |
| --- | --- |
| Palatinit | 10.0 |
| Zinc citrate | 0.1 |
| Sodium fluoride | 0.05 |
| (The concentration in terms of fluoride ion is 225 ppm) | |
| Sodium lauryl sulfate | 0.5 |
| Polyoxyethylene hydrogenated castor oil | 1.0 |
| Sodium dihydrogenphosphate | 0.1 |
| Disodium hydrogenphophate | 0.1 |
| Saccharin sodium | 0.1 |
| Flavor | 0.7 |
| Ethanol | 10.0 |
| Glycerol | 10.0 |
| Purified water | balance |
| Total | 100.0 |
| pH | 6.0 |

EXAMPLE 35 MOUTHWASH

A mouthwash was prepared by the following formulation according to the conventional procedures.

| Ingredients | Amounts % |
| --- | --- |
| Palatinit | 10.0 |
| Fine particle zinc oxide | 0.1 |
| (The average particle diameter is 0.3 μm: the specific surface area is 10 m$^2$/g) | |
| Sodium fluoride | 0.05 |
| (The concentration in terms of fluoride ion is 225 ppm) | |
| Sodium lauryl sulfate | 0.2 |
| Polyoxyethylene (2)-synthetic $C_{12}$, $C_{14}$ alkyl-sodium sulfosuccinate | 0.2 |
| Malic acid | 0.3 |
| Flavor | 0.7 |
| Glycerol | 10.0 |
| Xylitol | 5.0 |
| Purified water | balance |
| Total | 100.0 |
| pH | 7.5 |

EXAMPLE 36 GEL DENTIFRICE

A gel dentifrice was prepared by the following formulation according to the conventional procedures.

| Ingredients | Amounts % |
| --- | --- |
| Palatinit | 10.0 |
| Fine particle zinc oxide | 0.1 |
| (The average particle diameter is 0.3 μm: the specific surface area is 10 m$^2$/g) | |
| Sodium fluoride | 1.0 |
| (The concentration in terms of fluoride ion is 4,500 ppm) | |
| Phosphoric acid | 3.0 |
| Saccharin sodium | 0.5 |
| Flavor | 0.8 |
| Glycerol | 20.0 |
| Hydrochloric acid (2N) | 1.0 |
| Purified water | balance |
| Total | 100.0 |
| pH | 6.9 |

EXAMPLE 37 ORAL GEL

An oral gel was prepared by the following formulation according to the conventional procedures.

| Ingredients | Amounts % |
| --- | --- |
| Palatinit | 20.0 |
| Carboxymethyl cellulose | 0.2 |
| Fine particle zinc oxide | 0.1 |
| (The average particle diameter is 0.3 μm: the specific surface area is 10 m$^2$/g) | |
| Glycerol | 40.0 |
| Grape seed extract | 1.0 |
| α-tocopherol | 0.05 |
| Purified water | balance |
| Total | 100.0 |
| pH | 8.5 |

The present invention relates to an oral composition, which has the high safety, comprising either palatinit alone or in combination with fluorine compound, as well as an oral composition comprising palatinit in combination with zinc compound, which improves a bad feeling for use due to the zinc compound, and, by the inclusion of said ingredient, the present invention can provide an oral composition which can enhance remineralization.

The invention claimed is:

1. An oral composition for remineralization selected from the group consisting of a toothpaste, liquid dentifrice, gel, cream, mouthwash, spray, and foam comprising
    a combination of isomalt present in an amount of 0.1% to 60% of the total weight of the composition and a remineralization enhancing ingredient, wherein said remineralization enhancing ingredient is (A) a fluorine compound present in an amount of 100-1,100 ppm in terms of fluoride ion based on the total weight of the composition or (B) a water-slightly soluble zinc compound selected from the group consisting of zinc oxide, zinc citrate and zinc stearate that present in an amount of 0.1% to 5% of the total weight of the composition, and
    water
    and wherein said isomalt and said remineralization enhancing ingredient result in an increased remineralization value in comparison to the same ingredients of the composition except without the presence of isomalt.

2. The oral composition according to claim 1, comprising said fluorine compound as a remineralization enhancing ingredient.

3. The oral composition according to claim 2, wherein said fluorine compound is sodium fluoride.

4. The oral composition according to claim 1, comprising said water-slightly soluble zinc compound as a remineralization enhancing ingredient.

5. The oral composition according to claim 4, wherein said water-slightly soluble zinc compound is a powder having an average particle diameter of not greater than 0.3 μm and a specific surface area of greater than 10 m$^2$/g.

6. The oral composition according to claim 4, which has pH of 6.0-8.5.

7. The oral composition according to claim 6, wherein hydrochloric acid is used as a pH adjusting agent.

8. The oral composition according to claim 4, further comprising a fluorine compound.

9. The oral composition according to claim 8, wherein said fluorine compound is sodium fluoride.

10. A method of increasing remineralization in the teeth of a patient in need thereof comprising orally administering a composition of claim 1 to said patient, wherein an increased remineralization value results in comparison to administering the same ingredients of the composition except without the presence of isomalt.

11. A method of increasing remineralization in the teeth of a patient in need thereof comprising orally administering a composition of claim 9 to said patient, wherein an increased remineralization value results in comparison to the administering the same ingredients of the composition except without the presence of isomalt.

12. The oral composition according to claim 5, further comprising a fluorine compound.

13. The oral composition according to claim 12, wherein said fluorine compound is sodium fluoride.

* * * * *